US009864078B2

(12) United States Patent
Sumi et al.

(10) Patent No.: US 9,864,078 B2
(45) Date of Patent: Jan. 9, 2018

(54) PORTABLE TYPE RADIATION IMAGE CAPTURING APPARATUS

(71) Applicant: Konica Minolta, Inc., Chiyoda-ku, Tokyo (JP)

(72) Inventors: Makoto Sumi, Tokorozawa (JP); Manabu Kawaguchi, Hachioji (JP)

(73) Assignee: KONICA MINOLTA, INC., Chiyoda-Ku (JP)

( * ) Notice: Subject to any disclaimer, the term of this patent is extended or adjusted under 35 U.S.C. 154(b) by 0 days.

(21) Appl. No.: 14/646,540

(22) PCT Filed: Sep. 27, 2013

(86) PCT No.: PCT/JP2013/076300
§ 371 (c)(1),
(2) Date: May 21, 2015

(87) PCT Pub. No.: WO2014/080692
PCT Pub. Date: May 30, 2014

(65) Prior Publication Data
US 2015/0309194 A1    Oct. 29, 2015

(30) Foreign Application Priority Data

Nov. 21, 2012  (JP) .................... 2012-254822

(51) Int. Cl.
*G01T 7/00*   (2006.01)
*G03B 42/04*  (2006.01)
*A61B 6/00*   (2006.01)

(52) U.S. Cl.
CPC .............. *G01T 7/00* (2013.01); *A61B 6/4283* (2013.01); *A61B 6/4405* (2013.01); *G03B 42/04* (2013.01)

(58) Field of Classification Search
CPC ....................................................... G01N 23/05
(Continued)

(56) References Cited

U.S. PATENT DOCUMENTS 4,906,506 A * 3/1990 Nishimura ............... B29C 70/22
139/383 R
5,100,713 A * 3/1992 Homma .................. B29C 70/10
139/383 R
(Continued)

FOREIGN PATENT DOCUMENTS

JP    H0572657 A     3/1993
JP    2005313613 A   11/2005
(Continued)

OTHER PUBLICATIONS

International Search Report corresponding to Application No. PCT/JP2013/076300; dated Nov. 5, 2013, with English translation.
(Continued)

*Primary Examiner* — David Porta
*Assistant Examiner* — Djura Malevic
(74) *Attorney, Agent, or Firm* — Cantor Colburn LLP

(57) ABSTRACT

A portable type radiation image capturing apparatus may include a sensor panel which converts irradiated radiation to an electric signal and which obtains image data; and a case which stores the sensor panel and which is formed from material including carbon fiber. A foam body layer may be embedded in the case. The case may be formed so that a thickness of a layer on an outer side than the foam body layer is thicker than a thickness of a layer on an inner side than the foam body layer.

5 Claims, 4 Drawing Sheets

(58) Field of Classification Search
USPC .......................................................... 250/394
See application file for complete search history.

(56) References Cited

U.S. PATENT DOCUMENTS

| | | | | |
|---|---|---|---|---|
| 5,157,264 A | * | 10/1992 | Kinanen | G03B 42/04 250/484.4 |
| 5,441,251 A | * | 8/1995 | Ohta | G03B 42/02 206/449 |
| 5,783,278 A | * | 7/1998 | Nishimura | B29C 70/22 139/11 |
| 7,030,404 B2 | * | 4/2006 | Berger | G03B 42/045 250/589 |
| 7,135,222 B2 | * | 11/2006 | Nakano | C09K 11/7733 250/484.4 |
| 7,265,371 B2 | * | 9/2007 | Shoji | B32B 3/00 250/484.4 |
| 7,514,697 B2 | * | 4/2009 | Schindlbeck | G21K 4/00 250/484.4 |
| 7,576,335 B2 | * | 8/2009 | Shoji | G01T 1/202 250/483.1 |
| 2004/0146703 A1 | * | 7/2004 | Nakano | C09K 11/7733 428/292.1 |
| 2004/0159801 A1 | * | 8/2004 | Kishinami | C09K 11/628 250/484.4 |
| 2005/0077480 A1 | * | 4/2005 | Kishinami | G21K 4/00 250/484.4 |
| 2005/0260517 A1 | * | 11/2005 | Schindlbeck | G21K 4/00 430/139 |
| 2006/0283543 A1 | * | 12/2006 | Kubota | B29C 35/0266 156/272.2 |
| 2012/0089180 A1 | * | 4/2012 | Fathi | B41J 2/17559 606/214 |
| 2012/0153172 A1 | * | 6/2012 | Sumi | G01T 1/244 250/369 |
| 2012/0168632 A1 | * | 7/2012 | Yagi | A61B 6/4233 250/366 |
| 2012/0273687 A1 | * | 11/2012 | Nariyuki | G01T 1/20 250/366 |
| 2014/0121497 A1 | * | 5/2014 | Coppens | A61B 5/0555 600/415 |

FOREIGN PATENT DOCUMENTS

| | | | |
|---|---|---|---|
| JP | 2007020986 A | * | 2/2007 |
| JP | 2008170778 A | | 7/2008 |
| JP | 2008207523 A | | 9/2008 |
| JP | 2009020099 A | | 1/2009 |
| JP | 2009230000 A | | 10/2009 |
| JP | 2010160044 A | | 7/2010 |
| JP | 2011059058 A | * | 3/2011 |

OTHER PUBLICATIONS

English Translation of the International Preliminary Report on Patentability Chapter I and the Written Opinion of the International Searching Authority corresponding to Application No. PCT/JP2013/076300; dated May 26, 2015.

Notification of Refusal for corresponding JP Application No. 2014-548489; dated Jul. 4, 2017.

Chinese Notification of the First Office Action corresponding to Application No. 201380060241.9; dated Dec. 30, 2016, with English translation.

SIPO Office Action for corresponding CN Patent Application No. 201380060241.9, dated Aug. 30, 2017.

* cited by examiner

PORTABLE TYPE RADIATION IMAGE CAPTURING APPARATUS

CROSS REFERENCE TO RELATED APPLICATIONS

This is the U.S. national stage of application No. PCT/JP2013/076300, filed on Sep. 27, 2013. Priority under 35 U.S.C. §119(a) and 35 U.S.C. §365(b) is claimed from Japanese Application No. 2012-254822, filed Nov. 21, 2012, the disclosure of which is also incorporated herein by reference.

TECHNICAL FIELD

The present invention relates to a portable type radiation image capturing apparatus.

BACKGROUND ART

Conventionally, a computed radiography (CR) apparatus is widely used as an apparatus used in radiation image capturing for the purpose of diagnosis of disease. In such CR apparatuses, the energy of the radiation which passes the subject is accumulated in the photostimulable phosphor sheet. After capturing, the energy of the radiation accumulated in the photostimulable phosphor sheet is emitted as photostimulable light from the photostimulable phosphor sheet by scanning the photostimulable phosphor sheet with a laser light. The above is converted by photoelectric conversion with a photomultiplier tube, etc. to obtain image data to be used.

Usually, a cassette storing the photostimulable phosphor sheet inside is used in the CR apparatus. In order to load and use the cassette of the CR apparatus on a bucky apparatus (also called bucky capturing stage, etc., see later described FIG. 3) provided in a facility such as a hospital, etc., in which a conventional screen/film cassette is loaded, the cassette of the CR apparatus is usually designed and manufactured in a size similar to the JIS standard size of such screen/film cassette.

Lately, as a method of obtaining the medical radiation image, a radiation image capturing apparatus is developed in which the irradiated radiation is detected with photodiode, etc., to obtain the digital image data. Usually, the radiation image capturing apparatus includes a sensor panel in which a plurality of radiation detecting elements such as a photodiode which generates charge according to the dose of the irradiated radiation are arranged two dimensionally. Since the radiation is detected by a flat plate shaped sensor panel, the apparatus is also known as a flat panel detector (FPD).

Moreover, a cassette type radiation image capturing apparatus (in other words, a portable type radiation image capturing apparatus) in which the sensor panel is stored in a case and can be transported is also used in practice. Similar to the cassette for the CR apparatus, the portable type radiation image capturing apparatus is usually formed in a size conforming to the JIS standard size for the conventional screen/film cassette so that the portable type radiation image capturing apparatus can be loaded and used in an existing bucky apparatus without changing the bucky apparatus existing in a hospital, etc. to a new bucky apparatus (see, for example, Patent Literature 1).

Moreover, such portable radiation image capturing apparatus usually has a configuration so that the apparatus can be used without being loaded on the bucky apparatus. For example, the apparatus is usually configured so that the apparatus can be brought into the hospital room or home of the patient so as to be able to perform radiation image capturing in a state in which the apparatus is directly held against the body of the patient.

PRIOR ART DOCUMENT

Patent Literature

Patent Literature 1: Japanese Patent Application Laid-Open Publication No. 2010-160044
Patent Literature 2: Japanese Patent Application Laid-Open Publication No. 2005-313613
Patent Literature 3: Japanese Patent Application Laid-Open Publication No. 2009-230000

SUMMARY OF INVENTION

Problems to be Solved by the Invention

In such portable type radiation image capturing apparatus, for example, electronic components are included inside, and a glass substrate is used to protect the photodiode, etc. as described later. Therefore, the portable type radiation image capturing apparatus tends to become heavy compared to the cassette of the CR apparatus.

The shock applied to the portable type radiation image capturing apparatus when the apparatus hits somewhere becomes larger in the amount that the weight becomes heavier. For example, when the portable type radiation image capturing apparatus is used loaded on the bucky apparatus as described above, the portable radiation image capturing apparatus may hit the hard corner of the bucky apparatus. Moreover, for example, when the portable type radiation image capturing apparatus is used inserted between the patient and the bed, the portable type radiation image capturing apparatus may hit the hand rail or the corner of the bed. In such cases, the shock becomes larger.

In order to increase the shock resistance strength so that the case is not damaged even if the case receives such shock, examples of forming at least the case of the portable type radiation image capturing apparatus with a carbon plate in which carbon fiber is fixed with resin instead of simply plastic is increasing. However, typically, the carbon plate is heavier than plastic. Therefore, this becomes a reason for the weight of the portable type radiation image capturing apparatus becoming even heavier.

Therefore, in order to reduce the weight of the portable type radiation image capturing apparatus, although it is important to reduce the weight of the electronic component portion as much as possible and to make the glass substrate thinner to reduce the weight, it is also important to reduce the weight of the case of the portable type radiation image capturing apparatus. However, in order to reduce the weight of the case, when the thickness of the case is merely made thinner, the case is easily damaged such as breaking when the portable type radiation image capturing apparatus hits something else.

As shown in, for example, FIG. 5, it is well known that weight of a case 101 of a portable type radiation image capturing apparatus 100 can be reduced by embedding a foam body 103 formed from foam resin, etc. between carbon plates 102a and 102b composing the case 101 (for example, see patent literature 2, 3, etc.). In FIG. 5, the illustration of the glass substrate and the electronic components, etc. stored in the case 101 are omitted. As described in patent literature 2, 3, etc., it is possible to layer a plurality of carbon plates with the same thickness on the inner side and the outer side of the foam body 103.

However, according to such configuration, when the portable type radiation image capturing apparatus 100 hits something else, the carbon plate 102a of the outer layer of the case 101 may break and the case 101 may be damaged. If the number of carbon plates of the outer layer and the inner layer of the foam body 103 is increased to prevent the carbon plate 102a of the outer layer of the case 101 from being damaged, the entire case 101 becomes heavy. Moreover, when the portable type radiation image capturing apparatus is to be configured in the JIS size, the thickness of the portable type radiation image capturing apparatus cannot be made within the range of the thickness of the JIS size, which is 13 to 16 mm.

The present invention has been made in view of the above problems, and an object of the present invention is to provide a portable type radiation image capturing apparatus in which a weight of a case can be reduced while a surface of the case is able to maintain sufficient shock resistance strength.

Means for Solving the Problem

In order to solve the above-described problems, the invention according to Aspect 1 provides a portable type radiation image capturing apparatus including:

a sensor panel which converts irradiated radiation to an electric signal and which obtains image data; and a case which stores the sensor panel and which is formed from material including carbon fiber, wherein, a foam body layer is embedded in the case; and the case is formed so that a thickness of a layer on an outer side than the foam body layer is thicker than a thickness of a layer on an inner side than the foam body layer.

Advantageous Effects of Invention

According to the portable type radiation image capturing apparatus configured as a type as described in the present invention, a case is formed from a material including carbon fiber and a foam body layer is embedded in the case so that the case can be made lighter. In addition to the above, the case is configured so that the thickness of the outer layer on the outer side than the foam body layer in the case is thicker than the thickness of the inner layer on the inner side than the foam body layer (in other words, the foam body layer is placed on the inner side than the center in the case 2). With this, the thickness of the outer layer can be made thicker compared to when the outer layer and the inner layer are formed with the same thickness. Therefore, the thickness of the outer layer can be made thicker to enhance the shock resistance strength, etc. of the outer layer, and sufficient shock resistance strength of the surface of the case can be maintained without making the thickness of the entire case thicker.

EMBODIMENT FOR CARRYING OUT THE INVENTION

An embodiment of a portable type radiation image capturing apparatus of the present invention is described with reference to the drawings.

The portable type radiation image capturing apparatus described below is an indirect type radiation image capturing apparatus which includes a scintillator, etc. The indirect type radiation image capturing apparatus converts radiated radiation to an electromagnetic wave of another wavelength such as visible light, etc., converts the electromagnetic wave which was converted to an electric signal and obtains image data. Alternatively, the present invention can be applied to a direct type radiation image capturing apparatus which directly converts the radiation to the electric signal with the radiation detecting element without using the scintillator, etc., and obtains the image data.

Figure 1:
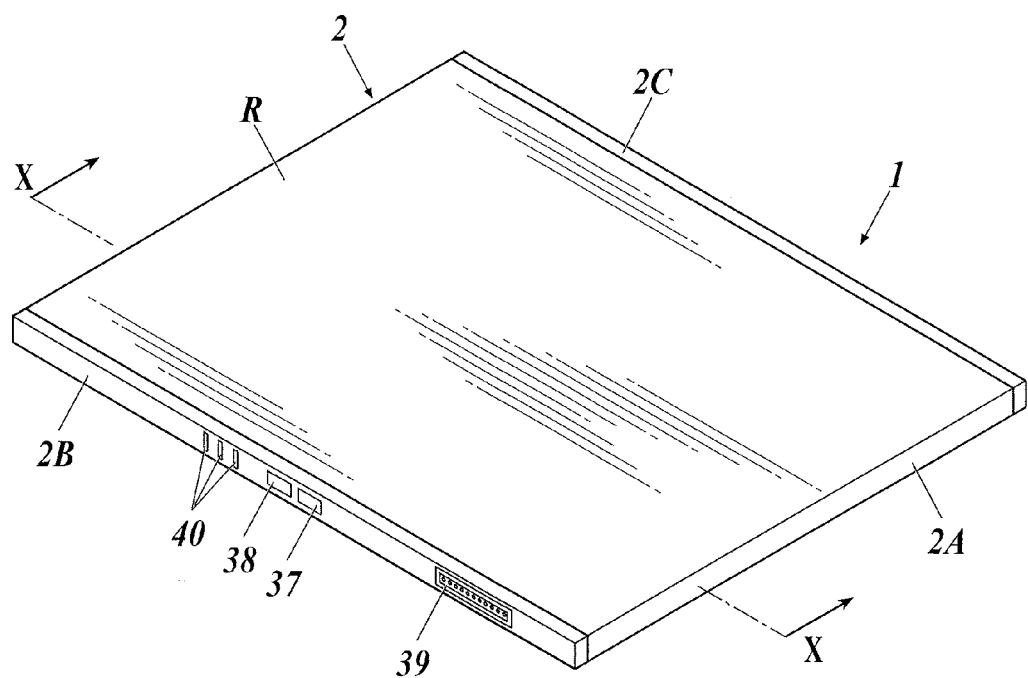
FIG. 1 is a perspective view showing an outer appearance of a portable type radiation image capturing apparatus of the present embodiment.
Figure 2:
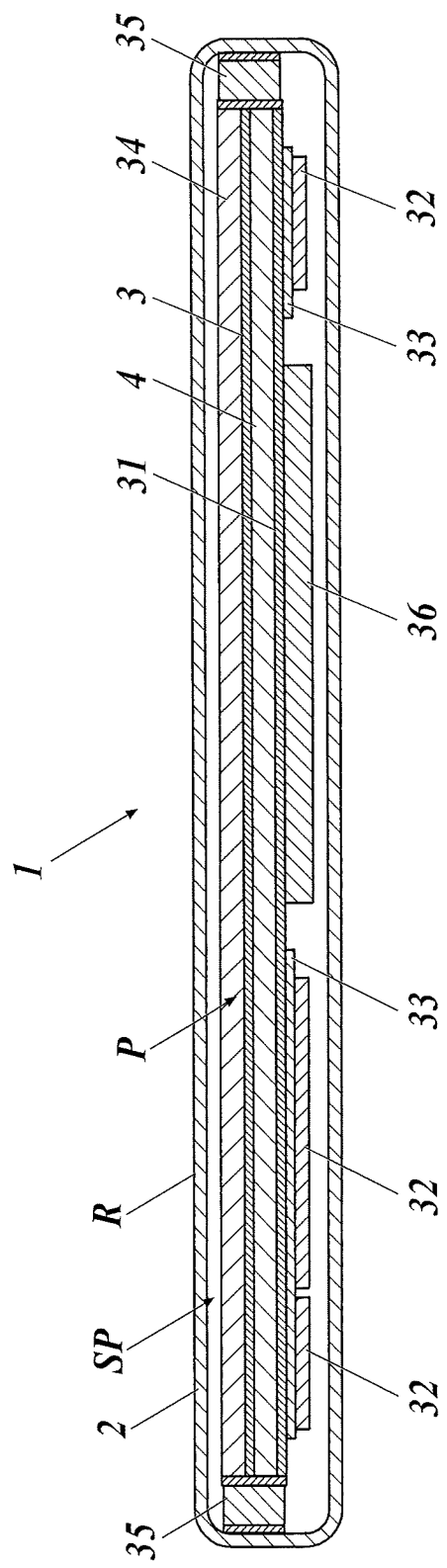
FIG. 2 is a cross-sectional view along line X-X shown in FIG. 1.

FIG. 1 is a perspective view showing an outer appearance of the portable type radiation image capturing apparatus of the present embodiment. FIG. 2 is a cross-sectional view along line X-X shown in FIG. 1. As shown in FIG. 1 and FIG. 2, the portable type radiation image capturing apparatus 1 stores a sensor panel SP in a case 2. The sensor panel SP is composed of a scintillator substrate 34 which is formed with a scintillator 3 on its surface, a sensor substrate 4 which detects visible light from the scintillator 3, and the like.

Regarding the case 2 of the present embodiment, the configuration of the hollow rectangular tube shaped case main body unit 2A which includes a radiation entering face R is described in detail later. The opening on both sides of the case main body unit 2A is blocked with lid members 2B and 2C to form the case 2.

The lid member 2B on one side of the case 2 is provided with the following, a power supply switch 37, a switching switch 38, a connector 39, and an indicator 40 including an LED, etc. displaying a battery state or operation state of the portable type radiation image capturing apparatus 1.

According to the present embodiment, although illustration is omitted, a connector provided at a tip of a cable can be connected to the connector 39, and for example, signals, etc. can be transmitted and received or image data, etc. can be transmitted between an external apparatus by wired methods through the connector 39. The battery 36 (not shown, see later described FIG. 2) of the portable type radiation image capturing apparatus 1 can be charged through the connector 39.

For example, although illustration is omitted, an antenna apparatus is provided in a lid member 2C, etc. on the opposite side of the case 2 so as to be embedded in the lid member 2C. According to the present embodiment, the portable type radiation image capturing apparatus 1 is able to receive and transmit signals, etc. wirelessly with an external device, etc. through the antenna apparatus.

Although illustration is omitted in FIG. 2, according to the present embodiment, a foam body layer 21 (see later described FIG. 4, etc.) is embedded in the case 2. However, this is described in detail later.

Moreover, a base 31 is provided in an internal space surrounded by the case 2. A sensor panel SP is provided on the radiation entering face R side (hereinafter simply referred to as upper face side) of the base 31 with a lead thin plate (not shown), etc. in between.

A PCB substrate 33 provided with an electronic component 32, etc. which drives the sensor panel SP and processes the signal output from the sensor panel SP, a battery 36, etc. are attached to the lower face side of the base 31. According to the present embodiment, a cushioning member 35 is provided between the sensor panel SP and the side face of the case 2.

Figure 3:
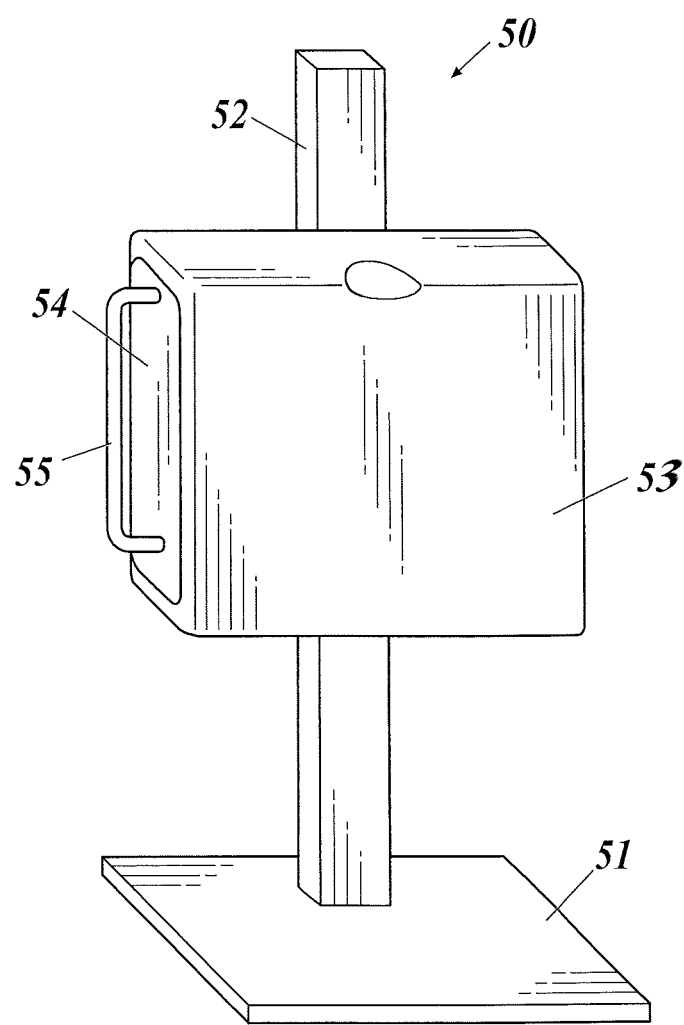
FIG. 3 is an outer appearance perspective view showing an example of a configuration of a bucky apparatus for capturing in a standing position as an example of a bucky apparatus.

Here, a bucky apparatus on which the portable type radiation image capturing apparatus 1 can be loaded to be used is described. FIG. 3 is an outer appearance perspective diagram showing an example of a configuration of a bucky apparatus for capturing in a standing position as an example of a bucky apparatus. The bucky apparatus 50 is composed with a cassette holder 53 (also called cassette holding unit) attached to a supporting pole 52 provided on a leg unit 51 so as to be able to move up and down. For example, a drawer unit 54 is provided with a handle unit 55 on a side face of the cassette holder 53 so that the portable type radiation image capturing apparatus 1 can be loaded inside.

According to the present embodiment, the case 2 of the portable type radiation image capturing apparatus 1 is formed in a size conforming to the JIS standard size (JIS Z 4905) of the screen/film cassette so that the portable type radiation image capturing apparatus 1 can be loaded on and used in a bucky apparatus 50 which is provided in a facility such as a hospital and in which the conventional screen/film cassette or cassette of the CR apparatus can be used, etc.

In other words, as described above, at least the thickness of the case 2 in the radiation entering direction (in other words, the direction orthogonal to the extending direction of the radiation entering face R (see FIG. 2) of the case 2) is formed to be within the range of 13 to 16 mm. The present invention can be applied to the portable type radiation image capturing apparatus which is not formed in the size conforming to the JIS standard size.

[Configuration Characteristic to Present Invention]

Next, the configuration to reduce the weight of the case 2 in the portable type radiation image capturing apparatus 1 of the present embodiment is described. Moreover, the function of the portable type radiation image capturing apparatus 1 of the present embodiment is also described.

According to the present embodiment, the case 2 storing the sensor panel SP is formed with material including carbon fiber. Similar to the portable type radiation image capturing apparatus 100 shown in FIG. 5 described above, according to the present embodiment also, the foam body layer is embedded in the case 2. However, according to the present embodiment, the case 2 is formed so that the thickness of the layer on the outer side than the foam body layer becomes thicker than the thickness of the layer on the inner side than the foam body layer. The above points are described in detail below.

Figure 4:
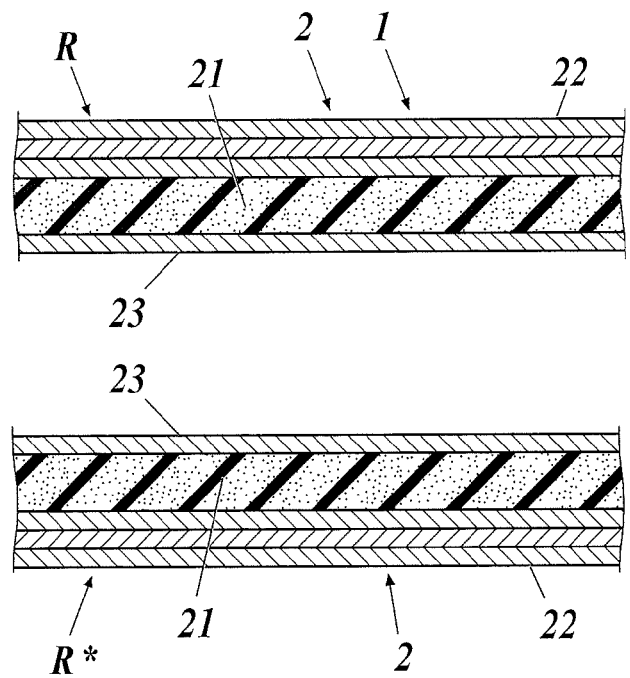
FIG. 4 is a cross sectional view for describing a state in which a foam body layer is embedded in a position toward an inner side than the center in the case.

According to the portable type radiation image capturing apparatus 1 of the present embodiment, as shown in FIG. 4, the case 2 (to be accurate, above described case main body unit 2A (see FIG. 1), the same applies to the following) is formed with an outer layer 22 layered on the outer side of the foam body layer 21, and an inner layer 23 layered on the inner side of the foam body layer 21.

Figure 5:
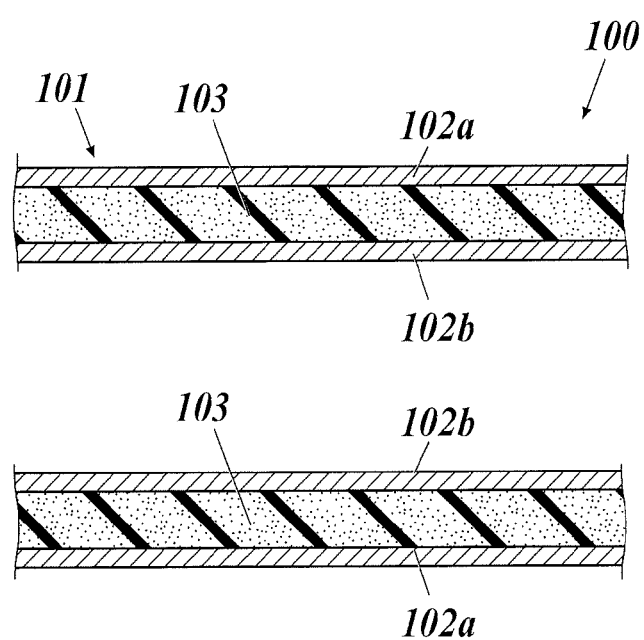
FIG. 5 is a cross-sectional view describing a state in which the foam body layer is embedded in the case of a conventional portable type radiation image capturing apparatus.

Similar to FIG. 5, the illustration of the sensor panel SP (see FIG. 2), etc. stored in the case 2 is omitted in FIG. 4. The relative thickness, length, size, etc. of each member do not always reflect the actual scale.

According to the above described portable type radiation image capturing apparatus 100 as shown in FIG. 5, the foam body layer 103 is embedded in exactly the center portion of the case 101. In other words, the case 101 is formed so that the thickness of the outer layer 102a on the outer side than the foam body layer 103 is substantially the same as the thickness of the inner layer 102b on the inner side than the foam body layer 103.

Therefore, for example, if the case 2 hits the corner of the cassette holder 53 or the handle 55 and shock is applied when the portable type radiation image capturing apparatus 1 is loaded in the cassette holder 53 (see FIG. 3) of the bucky apparatus 50, especially the outer layer 102a portion of the case 101 tends to break.

If the number of carbon plates layered with the outer layer 102a and the inner layer 102b of the case 101 is increased in the same number to make the thickness of the case 2 thicker in order to prevent the outer layer 102a of the case 101 from breaking as described in patent literature 2 and patent literature 3, the weight of the case 101 becomes heavy. Moreover, even if an attempt is made to form the case 2 of the portable type radiation image capturing apparatus 1 in the JIS standard size of the screen/film cassette, the case 101 becomes too thick and at least the thickness of the case 101 in the radiation entering direction cannot be made within the range of the JIS size of 13 to 16 mm.

As shown in FIG. 4, in the portable type radiation image capturing apparatus 1 of the present embodiment, the case 2 is composed so that the foam body layer 21 is embedded in a position toward the inner side than the center of the case 2. In other words, according to the portable type radiation image capturing apparatus 1 of the present embodiment, the case 2 is composed so that the thickness of the outer layer 22 on the outer side than the foam body layer 21 is thicker than the thickness of the inner layer 23 on the inner side than the foam body layer 21.

Therefore, for example, even if the thickness of the case 2, in other words, the total sum of the thickness of the outer layer 22, the foam body layer 21, and the inner layer 23 is the same, the thickness of the outer layer 22 can be made thicker compared to forming the thickness of the outer layer the same as the inner layer. With this, the thickness of the outer layer 22 can be made even thicker and the shock resistance strength, etc. of the outer layer 22 can be enhanced.

According to the present embodiment, as shown in FIG. 4, even if the case 2 is formed so that the foam body layer 21 is embedded in the case 2 in order to reduce the weight of the case 2, the shock resistance strength of the surface of the case 2 can be sufficiently maintained. Therefore, for example, even if the case 2 of the portable type radiation image capturing apparatus 1 hits the corner of the cassette holder 53, the handle 55 or the like and shock is applied, it is possible to reliably prevent the outer layer 22 of the case 2 from breaking.

The inventors found from research that according to the above configuration of the case 2, it is possible to sufficiently prevent the case 2 from damage when shock is applied in a degree such as simply hitting the bucky apparatus 50, etc. in normal capturing procedures.

FIG. 4 shows the foam body layer 21 formed on both the radiation entering face R side of the case 2 and the face R* on the opposite side. Alternatively, for example, the foam body layer 21 can be formed only on the face on the radiation entering face R side of the case 2 or only on the face R* on the other side of the case 2. Although illustration is omitted, the foam body layer 21 can be formed on the side face portion of the case 2.

The configuration of each unit composing the case 2 of the portable type radiation image capturing apparatus 1 of the present embodiment is described below. In order to maintain the shock resistance strength of the case 2, the foam body layer 21 is formed using a hard foam body with a base such as polymethacrylimide (PMI) which is very hard. According to the present embodiment, as described above, the case 2 is formed from material including carbon fiber, specifically, the outer layer 22 and the inner layer 23 of the case 2 are formed using prepreg known to be material including carbon fiber.

Then, as shown in FIG. 4, for example, the foam body layer 21 is layered on the outer side of the inner layer 23 formed with the prepreg and the outer layer 22 formed with the prepreg is layered on the further outer side. With this, it is possible to embed the foam body layer 21 in the case 2. The amount of prepreg layered as the outer layer 22 is larger than the prepreg layered as the inner layer 23. Therefore, the thickness of the outer layer 22 is made thicker than the thickness of the inner layer 23.

As the prepreg, it is well known that there is cross plied prepreg in which carbon fiber arranged in one direction is woven with carbon fiber arranged in the orthogonal direction, and unidirectional prepreg in which carbon fiber arranged in only one direction is included (for example, Japanese Patent Application Laid-Open Publication No. 2008-207523). The prepreg is formed by fixing the carbon fiber with, for example, resin.

Then, for example, the outer layer 22 of the case 2 is formed by combining the cross plied prepreg and the unidirectional prepreg. As described above, the carbon fiber has a very strong specific strength and has very strong pulling strength although it is light. Therefore, with the cross plied prepreg, even if strong pulling strength occurs in the face direction when hitting something, as long as the pulling strength is not unusually strong, the carbon fiber is not cut. Therefore, the cross plied prepreg is hardly damaged even when hitting something, and the shock resistance strength is very large.

Therefore, as shown in FIG. 4, preferably, the cross plied prepreg is positioned in the layer of the outer layer 22 which is the most outward when the outer layer 22 is formed on the outer side of the foam body layer 21 of the case 2. According to such configuration, the most outward layer of the outer layer 22 is formed with the cross plied prepreg. Therefore, the shock resistance strength of the surface of the case 2 can be made stronger. With this, for example, it is possible to make the case 2 so that even if the surface of the case 2 hits something, damage hardly occurs in the hit portion.

Although illustration is omitted, the unidirectional prepreg is formed by arranging the carbon fiber in the same direction and fixing the above with, for example, resin. With the unidirectional prepreg, even if strong pulling strength is applied in the extending direction of the carbon fiber, as long as the pulling strength applied to the carbon fiber is not strong enough to cut the carbon fiber, the carbon fiber is hardly extended. Therefore, the unidirectional prepreg has the feature of becoming difficult to bend in the extending direction of the carbon fiber.

For example, preferably, if a portion of the unidirectional prepreg forming the outer layer 22 and the inner layer 23 of the case 2 is provided so that the extending direction of the carbon fiber is in a longitudinal direction (in other words, for example, the direction from one X to the other X in FIG. 1) of the case 2, the case 2 of the portable type radiation image capturing apparatus 1 hardly bends in the longitudinal direction.

For example, by forming the case 2 so that a plurality of the unidirectional prepreg are provided so that the extending direction of the carbon fiber is in a direction orthogonal to each other (see above described Japanese Patent Application Laid-Open Publication No. 2008-207523) or the extending direction of the carbon fiber forms an angle of 45°, etc. (see above described Japanese Patent Application Laid-Open Publication No. 2004-70253), the case 2 hardly bends in various directions. With this, it is possible to enhance the stiffness of the case 2.

[Effect] As described above, according to the portable type radiation image capturing apparatus 1 of the present embodiment, the case 2 which stores the sensor panel SP is formed from material including carbon fiber. The foam body layer 21 is embedded in the case 2 and the thickness of the outer layer 22 on the outer side than the foam body layer 21 in the case 2 is formed to be thicker than the thickness of the inner layer 23 on the inner side than the foam body layer 21.

As described above, the case 2 is made so that the thickness of the outer layer 22 on the outer side than the foam body layer 21 becomes thicker than the thickness of the inner layer 23 on the inner side than the foam body layer 21 (in other words, the foam body layer 21 is placed toward the inner side than the center in the case 2). Therefore, for example, compared to when the outer layer is formed with the same thickness than the inner layer, the thickness of the outer layer 22 can be made even thicker. Therefore, the thickness of the outer layer 22 can be made thicker so that the shock resistance strength of the outer layer 22 can be enhanced, and the shock resistance strength of the surface of the case 2 can be sufficiently maintained even if the entire thickness of the case 2 is not made thick.

As described above, according to the portable radiation image capturing apparatus 1 of the present embodiment, the case 2 is formed from material including carbon fiber and the foam body layer 21 is embedded in the case 2. With this, the case 2 can be made lighter and the shock resistance strength of the surface of the case 2 can be maintained to a sufficient strength so that the case 2 is not damaged when hitting something during normal use. Consequently, the portable radiation image capturing apparatus 1 can be made light, strong and easy to use.

In the embodiment described above, the foam body layer 21 of the case 2 is formed from a hard foam body with PMI as the base. Alternatively, the foam body layer 21 can be formed using the foam body other than the foam body with PMI as the base. Specifically, regarding the hard plastic foam body, a foam body which is harder or lighter (or cheaper) may be developed with modifications in quality and material, and such foam body can be used and the present invention can be applied when such foam body is used.

The present invention is not limited to the above described embodiment, and the present invention can be suitably changed without leaving the scope of the present invention.

INDUSTRIAL APPLICABILITY

The present invention can be used in the field of radiation image capturing (specifically, medical field).

The invention claimed is:

1. A portable type radiation image capturing apparatus comprising:
    a sensor panel which converts irradiated radiation to an electric signal and which obtains image data; and
    a case which stores the sensor panel and which is formed from material including carbon fiber, the case comprising a case wall separating an interior of the apparatus from an exterior of the apparatus, the case wall comprising:
    an outer layer located at an exterior side of the case wall;
    an inner layer located at an interior side of the case wall; and
    a foam body layer between the inner layer and the outer layer;
    wherein an outer layer thickness is greater than an inner layer thickness.

2. The portable type radiation image capturing apparatus of claim 1, wherein, the case is formed in a size conforming to a JIS standard size for a screen/film cassette.

3. The portable type radiation image capturing apparatus of claim 1, wherein an outer layer of the case comprises a combination of a cross plied prepreg and a unidirectional prepreg; and
    the cross plied prepreg is positioned in a layer of the outer layer which is most outward when the outer layer is formed on the outer side of the foam body layer.

4. The portable type radiation image capturing apparatus of claim 3, wherein a portion of the unidirectional prepreg and an inner layer of the case are provided so that an extending direction of the carbon fiber is in a longitudinal direction.

5. The portable type radiation image capturing apparatus of claim 1, wherein the case comprising a stack of layers fully surrounding internal components of the portable type radiation image capturing apparatus.

* * * * *